United States Patent
Hoffman

(10) Patent No.: US 11,696,741 B2
(45) Date of Patent: *Jul. 11, 2023

(54) VISUALLY OPTIMIZED INTRAVASCULAR IMAGING AND ASSOCIATED DEVICES, SYSTEMS, AND METHODS

(71) Applicant: PHILIPS IMAGE GUIDED THERAPY CORPORATION, San Diego, CA (US)

(72) Inventor: Joseph Hoffman, Sacramento, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 71 days.

This patent is subject to a terminal disclaimer.

(21) Appl. No.: 17/331,172

(22) Filed: May 26, 2021

(65) Prior Publication Data

US 2021/0275137 A1  Sep. 9, 2021

Related U.S. Application Data

(63) Continuation of application No. 14/537,967, filed on Nov. 11, 2014, now Pat. No. 11,020,087.

(Continued)

(51) Int. Cl.
*A61B 8/12* (2006.01)
*A61B 5/00* (2006.01)
(Continued)

(52) U.S. Cl.
CPC .............. *A61B 8/12* (2013.01); *A61B 5/0066* (2013.01); *A61B 5/0215* (2013.01);
(Continued)

(58) Field of Classification Search
None
See application file for complete search history.

(56) References Cited

U.S. PATENT DOCUMENTS

| 5,315,999 A | 5/1994 | Kinicki |
| 5,967,985 A | 10/1999 | Hayakawa |

(Continued)

FOREIGN PATENT DOCUMENTS

| CN | 102551810 A | 7/2012 |
| JP | 2006020944 A | 1/2006 |

(Continued)

OTHER PUBLICATIONS

International Searching Authority/United States Patent Office, Notification of Trasnmittal of the International Search Reort and the Written Opinion of the International Searching Authority or the Declartion for PCT/US2014/064769, dated Feb. 13, 2015.

*Primary Examiner* — Luther Behringer
*Assistant Examiner* — Marjan Saboktakin

(57) ABSTRACT

Intravascular devices, systems, and methods are disclosed. In some embodiments, a medical imaging system for imaging vasculature of a patient is provided. The imaging system includes a console that has one or more processors with a medical imaging system interface running thereon, an acquisition card in communication with the one or more processors and in communication with a patient interface module (PIM), and an intravascular imaging component in communication with the PIM and disposed on a distal end of a flexible elongate member. The medical imaging system interface provides a plurality of settings groups for selection by a user, each of the settings groups having pre-acquisition parameters and post-acquisition parameters that are optimal for imaging a desired viewing target within the vasculature. Associated methods and computer-readable media are provided.

15 Claims, 5 Drawing Sheets

Related U.S. Application Data

(60) Provisional application No. 61/903,764, filed on Nov. 13, 2013.

(51) Int. Cl.
*A61B 5/1459* (2006.01)
*A61B 5/0215* (2006.01)

(52) U.S. Cl.
CPC ............ *A61B 5/1459* (2013.01); *A61B 5/743* (2013.01); *A61B 5/748* (2013.01); *A61B 5/7435* (2013.01); *A61B 5/0037* (2013.01)

(56) References Cited

U.S. PATENT DOCUMENTS

| | | |
|---|---|---|
| 6,063,030 A | 5/2000 | Vara |
| 6,142,940 A | 11/2000 | Lathbury |
| 2002/0168618 A1 | 11/2002 | Anderson |
| 2006/0241469 A1 | 10/2006 | Rold |
| 2007/0232907 A1 | 10/2007 | Pelissier |
| 2007/0239010 A1 | 10/2007 | Johnson |
| 2008/0130972 A1 | 6/2008 | Miller |
| 2010/0049046 A1 | 2/2010 | Peiffer |
| 2010/0174190 A1 | 7/2010 | Hancock |
| 2012/0065511 A1 | 3/2012 | Jamello |
| 2013/0011034 A1 | 1/2013 | Glynn |
| 2014/0100449 A1 | 4/2014 | Begin |
| 2015/0182188 A1 | 7/2015 | Cori |

FOREIGN PATENT DOCUMENTS

| | | |
|---|---|---|
| JP | 2007301122 A | 11/2007 |
| WO | 2007023433 A1 | 3/2007 |
| WO | 2010104775 A1 | 9/2010 |
| WO | 2012138874 A1 | 12/2012 |

VISUALLY OPTIMIZED INTRAVASCULAR IMAGING AND ASSOCIATED DEVICES, SYSTEMS, AND METHODS

CROSS REFERENCE TO RELATED APPLICATION

The present application is a continuation of U.S. patent application Ser. No. 14/537,967, filed Nov. 11, 2014, now U.S. Pat. No. 11,020,087, which claims priority to and the benefit of the U.S. Provisional Patent Application No. 61/903,764, filed Nov. 13, 2013, each of which is hereby incorporated by reference in its entirety.

TECHNICAL FIELD

The present disclosure is related to medical imaging systems as used in the treatment of various maladies. In particular, embodiments disclosed herein are particularly suited for use in intravascular and intracardiac imaging and treatment systems.

BACKGROUND

Heart disease is one of many serious conditions that can require emergency operations to save lives. A main cause of heart disease is the accumulation of plaque inside the blood vessels, which eventually occludes the blood vessels. Common treatment options available to open up the occluded vessel include balloon angioplasty, rotational atherectomy, and intravascular stents. Clinicians may rely on intravascular imaging systems to observe and characterize conditions in order to determine the best course of treatment. Other conditions also necessitate investigations within a patient's body.

Some of these techniques, like intravascular ultrasound (IVUS) and optical coherence tomography (OCT), may utilize intravascular devices like catheters and guidewires. Often intravascular catheters and guidewires are utilized to visualize the inner lumen of the blood vessel. Such catheters and guidewires contain imaging elements and may also contain other electronic, optical, or electro-optical components. Obtaining useful images from within the vasculature of a patient by imaging sensing devices has a number of difficulties. The structures and features to be visualized in a target area can have significantly different properties which may respond very differently to a visualization mechanism such as ultrasound. For example, the ultrasonic backscatter from a stent is very different that from soft tissue or plaque. The different reactions complicate visualization of either type of feature in a target area.

Accordingly, there remains a need for improved intravascular devices, systems, and methods that can provide useful imaging data from the varied features to be observed within a target area.

SUMMARY

Embodiments of the present disclosure are directed to intravascular devices, systems, and methods.

In one embodiment, a method for optimally viewing medical images is provided. The method includes steps of positioning a medical imaging device into vasculature of a patient at an area of interest and selecting a desired settings group from a plurality of settings groups in a medical imaging system interface that provides control over the medical imaging device. The medical imaging device is in communication with a medical imaging system, and the desired settings group includes parameters affecting acquisition over an acquisition pipeline of the medical imaging system. The method further includes a step of collecting imaging data at the area of interest using the medical imaging device.

In another embodiment, a medical imaging system for imaging vasculature of a patient is provided. The imaging system includes a console that has one or more processors with a medical imaging system interface running thereon, an acquisition card in communication with the one or more processors and in communication with a patient interface module (PIM), and an intravascular imaging component in communication with the PIM and disposed on a distal end of a flexible elongate member. The medical imaging system interface provides a plurality of settings groups for selection by a user, each of the settings groups having pre-acquisition parameters and post-acquisition parameters that are optimal for imaging a desired viewing target within the vasculature.

In yet another embodiment, a computer-readable medium including instructions is provided. The instructions when executed by one or more processors of an medical imaging system, causes the medical imaging system to perform a method for optimally viewing medical images. The method includes steps of selecting a desired settings group from a plurality of settings groups in a medical imaging system interface that provides control over the medical imaging device, propagating the parameters of the desired settings group to components of the acquisition pipeline, collecting imaging data at the area of interest using the medical imaging device. The desired settings group includes parameters affecting acquisition over an acquisition pipeline of the medical imaging system.

Additional aspects, features, and advantages of the present disclosure will become apparent from the following detailed description.

These and other embodiments will be described in further detail below with respect to the following figures.

Figure 1:
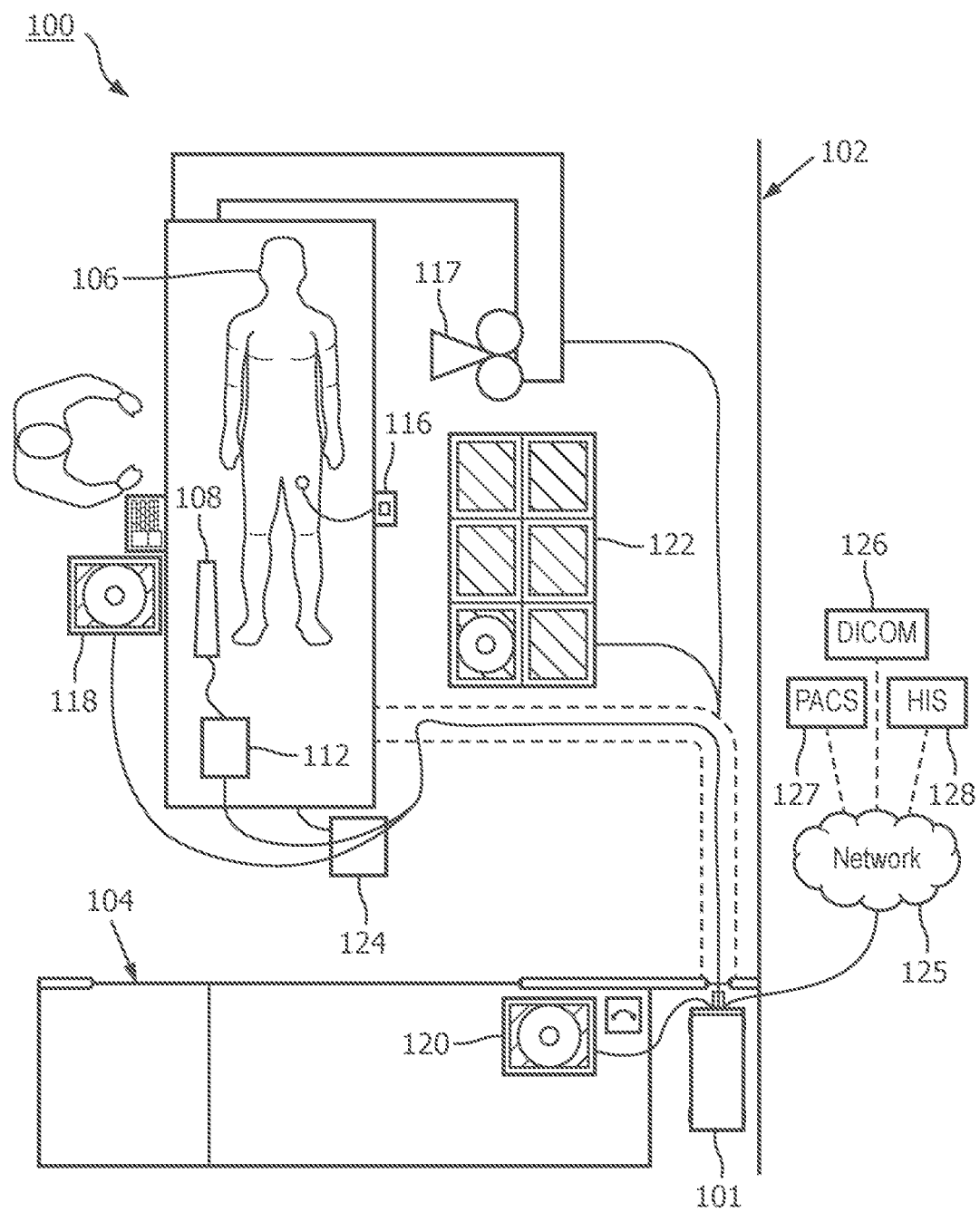
FIG. 1 is diagram of a medical imaging system according to some embodiments of the present disclosure.

For clarity of discussion, elements having the same designation in the drawings may have the same or similar functions. The drawings may be better understood by referring to the following Detailed Description.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram depicting a medical imaging system 100. In general, the medical imaging system 100 provides for coherent acquisition, integration, and consolidation of multiple forms of acquisition and processing elements designed to be sensitive to a variety of methods used to acquire and interpret human biological physiology and morphological information and to coordinate treatment of various conditions. In one embodiment, the medical system 100 includes a processing system 101 that is a computer system with the hardware and software to acquire, process, and display medical data, but, in other embodiments, the processing system 101 may be any other type of computing system operable to process medical data. In the embodiments in which processing system 101 is a computer workstation, the system includes at least one processor such as a microcontroller or a dedicated central processing unit (CPU), a non-transitory computer-readable storage medium such as a hard drive, random access memory (RAM), and/or compact disk read only memory (CD-ROM), a video controller such as a graphics processing unit (GPU), and a network communication device such as an Ethernet controller or wireless communication controller.

In some embodiments, the processing system 101 is programmed to execute steps associated with the medical image acquisition, analysis, and control described herein. Accordingly, it is understood that any steps related to data acquisition, data processing, instrument control, and/or other processing or control aspects of the present disclosure may be implemented by the processing system 101 using corresponding instructions stored on or in a non-transitory, computer-readable medium accessible by the processing system. In some instances, the processing system 101 is portable (e.g., handheld, on a rolling cart, etc.). Further, it is understood that in some instances processing system 101 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

In the depicted embodiment, the medical imaging system 100 is deployed in a catheter lab 102 having a control room 104, with the processing system 101 being located in the control room. In other embodiments, the processing system 101 may be located elsewhere, such as inside the catheter lab 102, in a centralized area in a medical facility, or at an off-site location accessible by an extended network. The catheter lab and control room may be used to perform on a patient any number of medical sensing procedures known in the art. A patient 106, depicted in catheter lab 102, may be undergoing a single modality or multi-modality procedure either as a single procedure or in combination with one or more sensing procedures. For example, an angioplasty procedure may be performed to position a stent in a target location in a target region of the vasculature of the patient 106.

In the illustrated embodiment of FIG. 1, intravascular device 108 is a medical imaging device that may be utilized by a clinician to acquire medical imaging data about the patient 106 and/or to provide a treatment to the patient 106. For instance, the intravascular device 108 may images by using ultrasound (e.g., IVUS), OCT, thermal, and/or other imaging techniques. The intravascular device 108 may be any form of device, instrument, catheter, or probe that is sized and shaped to be positioned within a vessel. In some embodiments, intravascular device 108 may be combined with a non-imaging component into a single package that is sized and shaped to be positioned within a vessel. As illustrated, the IVUS instravascular device 108 is an IVUS catheter that includes one or more sensors such as a phased-array transducer to collect IVUS sensing data. In some embodiments, the intravascular device 108 may be capable of multi-modality sensing such as both IVUS and intravascular photoacoustic (IVPA) sensing, or OCT and IVUS sensing, etc.

In the depicted embodiment, a patient interface module (PIM) 112 couples the intravascular device 108 to the medical imaging system 100. The PIM 112 facilitates the exchange of information between the intravascular device 108 and the processing system 101, serving as a medical device interface therebetween. This information includes imaging data transmitted from the intravascular device 108 to the processing system 101 and commands and settings, which may include individual parameter specifications, communicated from the processing system 101 to the PIM 112 and to the intravascular device 108 itself. Thus, the PIM 112 is operable to receive medical imaging and/or sensing data collected from the patient 106 using the intravascular device 108 and to transmit the received data to a processing system such as the processing system 101.

In the depicted embodiment, the PIM 112 includes analog-to-digital (A/D) and/or digital-to-analog (D/A) converters and transmits digital data to the processing system 101 and analog signals to the imaging device 108. However, in other embodiments, the PIM 112 may transmit and receive analog and/or digital data to and from the processing system 101 and/or the imaging device 108. In one embodiment, the imaging PIM 112 transmits medical imaging data and/or receives commands over a high-speed data bus connection or a high-speed wireless networking standard. In embodiments where PIM 112 incorporates a user interface, commands may be received through the user interface rather than from a networked source.

A bedside controller 118 is also communicatively coupled to the processing system 101 and provides user control of the particular medical modality (or modalities) being used to diagnose the patient 106. In the current embodiment, the bedside controller 118 is a touch screen controller that provides user controls and diagnostic images on a single surface within the field of operation. In alternative embodiments, however, the bedside controller 118 may include both a non-interactive display and separate controls such as physical buttons and/or a joystick, and/or a keyboard and mouse. In the integrated medical imaging system 100, the bedside controller 118 is operable to present control options for the intravascular device 108 and patient imaging data collected therefrom in graphical user interfaces (GUIs).

Additionally, the controller 118 may be coupled to the PIM 112 to communicate with it over a high-speed wired or wireless connection or link.

The medical imaging system 100 provides a medical imaging system interface by which a variety of settings groups may be selected from by a user. The settings groups include a plurality of parameters that are pre-set in order to optimize the viewing of specific features at a target area. More detail regarding the settings groups and the selection thereof is provided later in this disclosure.

A main controller 120 in the control room 104 adjacent to the catheter lab 102 is also communicatively coupled to the processing system 101 and/or the PIM 112. In the current embodiment, the main controller 120 is similar to the bedside controller 118 in that it includes a touch screen and is operable to display a multitude of GUI-based controls corresponding to different medical sensing modes via a UI framework service executing thereon. In alternative embodiments, the main controller 120 may include a non-interactive display and standalone controls such as a mouse and keyboard. In some embodiments, the processing system 101 may be absent, such that the intravascular device 108 is controlled only through the bedside controller 118 and/or the main controller 120. In such an embodiment, the imaging data collected is at least temporarily stored in the controller 118 and/or 120.

Thus, while in the depicted embodiment PIM 112 is in communication with the processing system 101 as described above, in some embodiments, the bedside controller 118 receives data from and communicates commands to PIM 112 instead. And in some embodiments, the main controller 120 additionally or alternatively receives data from and communicates commands to PIM 112.

Figure 2:
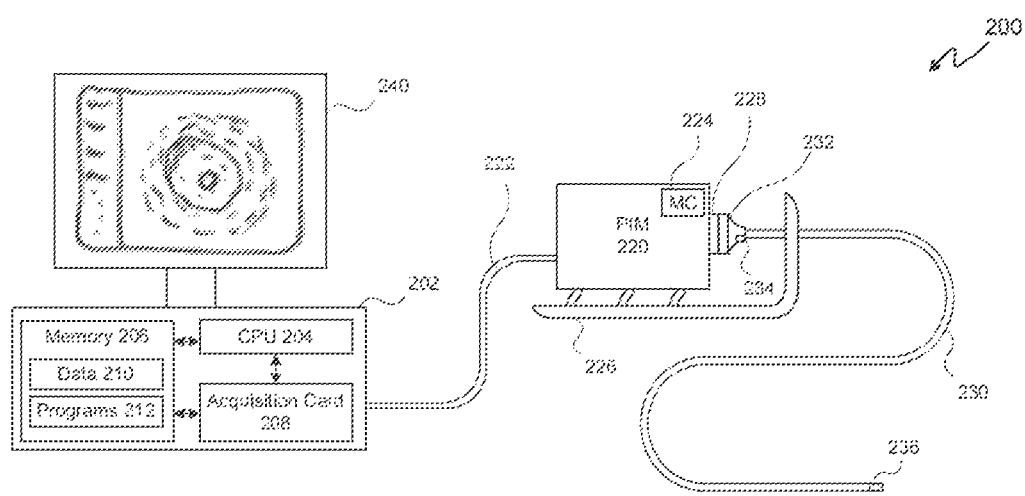
FIG. 2 is a diagram of another medical imaging system according to some embodiments of the present disclosure.

Referring to FIG. 2, shown therein is an alternative medical imaging system 200 that shares a number of features with the medical imaging system 100 described above in connection with FIG. 1. The medical imaging system 200 may be understood as a subset of the medical imaging system 100, while generally having the same capabilities when collecting, processing, and viewing imaging data from a patient. The medical imaging system 200 includes a controller 202, which may be a workstation-type controller or may be a hand-held computing device such as a tablet computing device. The controller 202 includes one or more processors, illustrated as central processing unit (CPU) 204, in communication with a memory 206 and an acquisition card 208, which may include a plurality of analog components and field-programmable gate arrays.

The memory 206 may include multiple types of memory and/or multiple levels of memory. Thus, memory 206 may include random access memory (RAM), read only memory (ROM), a hard disk drive, a solid-state drive, etc. The memory 206 stores data 210, which may include imaging data collected using an intravascular device and parameter settings therefor, and programs 212, which may provide for imaging data collection, for the manipulation of collected data, and for the selection and implementation of settings and parameters associated with the imaging collection process and devices.

The acquisition card 208 provides an interface between the controller 202 and a PIM 220, being coupled thereto by a high-speed link 222. In some embodiments, more than one acquisition card may be present in the medical imaging system 200. For example, acquisition card 208 may be present on the controller 202, while another is present in the PIM 220 or in a bedside box, such as the beside controller 118 of FIG. 1. The PIM 220 includes a processor or microcontroller (MC) 224 that facilitates communication with and control of an imaging device 230, such as an IVUS catheter or intravascular device. The PIM 220 includes a sled 226 that can be used to move the PIM 220 and thereby the imaging device 230 during controlled translational movements, such as a "pullback" movement. The PIM 200 includes a device socket 228 that is used to couple the imaging device 230 to the PIM 200. The imaging device 230 includes a coupler 232 at its proximal end, which is inserted into the socket 228 to communicatively and physically secure the imaging device 230 to the PIM 220. In some embodiments, the imaging device 230 may be a rotational IVUS catheter. In such embodiments, the socket 228 is configured to rotate to provide for the rotation of the coupled imaging device 230.

The imaging device 230 further includes a chip 234. In some embodiments, the chip includes a ROM, such as an erasable programmable ROM (EPROM), that includes information regarding the imaging device 230, such as an identifier of the type of device it is. The chip 234 may further include parameters for settings, like gain, that may be implemented on the imaging device 230. The parameters may be changed by communication through the PIM 220. In some embodiments, the chip 234 is a microcontroller that can communicate with the PIM 220 in the control of an imaging component 236 disposed at a distal end of the imaging device 230 and in receiving data therefrom. The chip 234 is illustrated as being included in the coupler 234, but in other embodiments may be located elsewhere within the imaging device 230 and/or the PIM 220.

Figure 3:
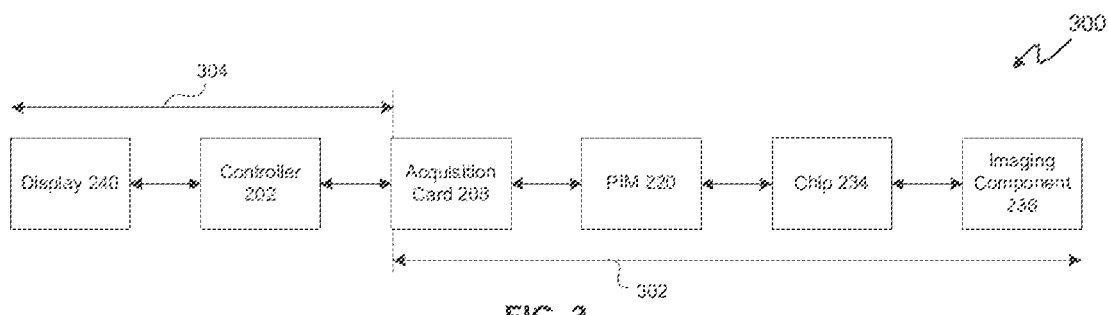
FIG. 3 is a diagram of an imaging pipeline such is present in the medical imaging systems of FIGS. 1 and 2 according to some embodiments of the present disclosure.

Referring now to FIG. 3, the collection of imaging data from the imaging component 236 may include the application of many different settings parameters and processing along the imaging pipeline 300. The pipeline 300 extends from the imaging component 236 where data is collected all the way to a display 240 (coupled to the controller 202). The pipeline thus includes the imaging component 236, the chip 234, the PIM 220, the acquisition card 208, and the CPU 205, which may apply additional settings-associated processing by the programs 212 running thereon. In some embodiments, a many different settings may be controlled by various parameters. The settings may include several different gain settings, time gain compensation (TGC) settings, contrast settings, and various filter settings.

Beginning at the imaging component side and working through the pipeline 300, some of the controllable settings include transmit pulse frequency and shape, transmit pulse amplitude, coded transmit sequence, coded transmit frequency, coded transmit amplitude, transmit sequencing for arrays, pulse repetition frequency. The controllable settings also may include PIM rotational speed, PIM pullback speed, array beam forming and focusing, array apodization, digitization rate, frame rate, field-of-view, coherent data averaging (whether a-line based or frame-based), and bandpass filtering (analog or digital) to remove high-frequency noise and low-frequency drift, ringdown removal ON/OFF, ringdown removal settings, non-linear rank filter settings, envelope detection settings, dynamic range, saturation, blood flow detection settings (sensitivity, thresholds, and Doppler settings), compression settings, persistence, and other recursive filter settings, color mapping settings.

This large number of settings that may be controlled by varying parameters through the pipeline 300 can complicate the selection of appropriate parameters for a clinician during a given surgical procedure. The pipeline 300 may be understood as having two main stages: a pre-acquisition stage 302 and a post-acquisition stage 304 as illustrated in FIG. 3. The pre-acquisition stage 302 and the post-acquisition stage both include many settings and may include sequential settings of a single type. For example, the pipeline 300 may include a gain setting at the chip 234, another gain setting at the PIM 220, and yet another gain setting implemented by the acquisition card 208. While the gain settings at each of the pipeline-components may serve similar functions, they are not necessarily fungible. Thus, the application of a certain level of gain at the PIM 220 may have some differences if a similar level of gain were to be applied at the acquisition card 208. In some embodiments, the post-acquisition stage 304 may include some of the features provided by the acquisition card 208, while the pre-acquisition stage 302 includes some other features provided thereby.

Allowing a user access to individually adjust each parameter in pipeline components of the pre-acquisition stage 302 and the post-acquisition stage 304 could complicate the operation enough to make an imaging system like the system 200 too difficult to use in an effective manner for different types of evaluations. However, if control of the settings is not presented to the user, the full capabilities of the imaging system are not realized. Further, when imaging data is collected from imaging component 236, the imaging data passes through the pipeline 300. After the processed data leaves the acquisition card 208, it may be processed further by programs 212 running on the CPU 204 and/or it may be stored for later viewing and analysis. In general, after imaging data is stored in memory 206 or in networked storage, only some of the processing may be "undone". The software processing performed by the programs 212 may be performed using different settings, but the settings applied during the pre-acquisition stage will limit the available adjustments.

Certain features at a target area within a patient may be better viewed by having certain settings applied. For instance at a particular target area within a patient, it may be useful to view both a stent and atherosclerotic plaque. Given the different properties of these two imaging subjects, different settings may be needed to image both in detail. For example, because the stent may reflect ultrasound energy much more readily than plaque does, a relatively lower gain setting may improve the useful detail in obtained images.

Also, certain filter stages may be better for one imaging subject than another. For example, aggressive filtering of the signal may lower the noise level and permit the visualization of plaque, plaque borders, or thrombus. However, the corresponding decrease in bandwidth may compromise the axial resolution and degrade the ability to visualize stents. Filters are used throughout the pipeline to achieve various goals. The analog and digital filters near the front of the pipeline 300 may limit the signal bandwidth in order to reduce noise. In some situations, a user may be willing to accept more noise, to get more bandwidth as it may provide improved image resolution. Or, the user might want to reduce noise at the expense of bandwidth. Filters later in the pipeline may serve other purposes such as envelope detection of the signal and "persistence". Persistence may smooth moving images by performing a frame-to-frame weighted average. Thus, providing appropriate control to a user of a medical imaging system, like medical imaging systems 100 and 200, may facilitate the collection of more detailed, accurate imaging data.

One of the programs 212 running on the CPU 204 of the controller 202 of FIG. 2 or the bedside controller 118 or the main controller 120 of FIG. 1 provides a medical imaging system interface to facilitate the appropriate control of settings that may be applied in the imaging pipeline 300. Embodiments of such a medical imaging system interface are illustrated in FIGS. 4 and 5 and described below.

Figure 4:
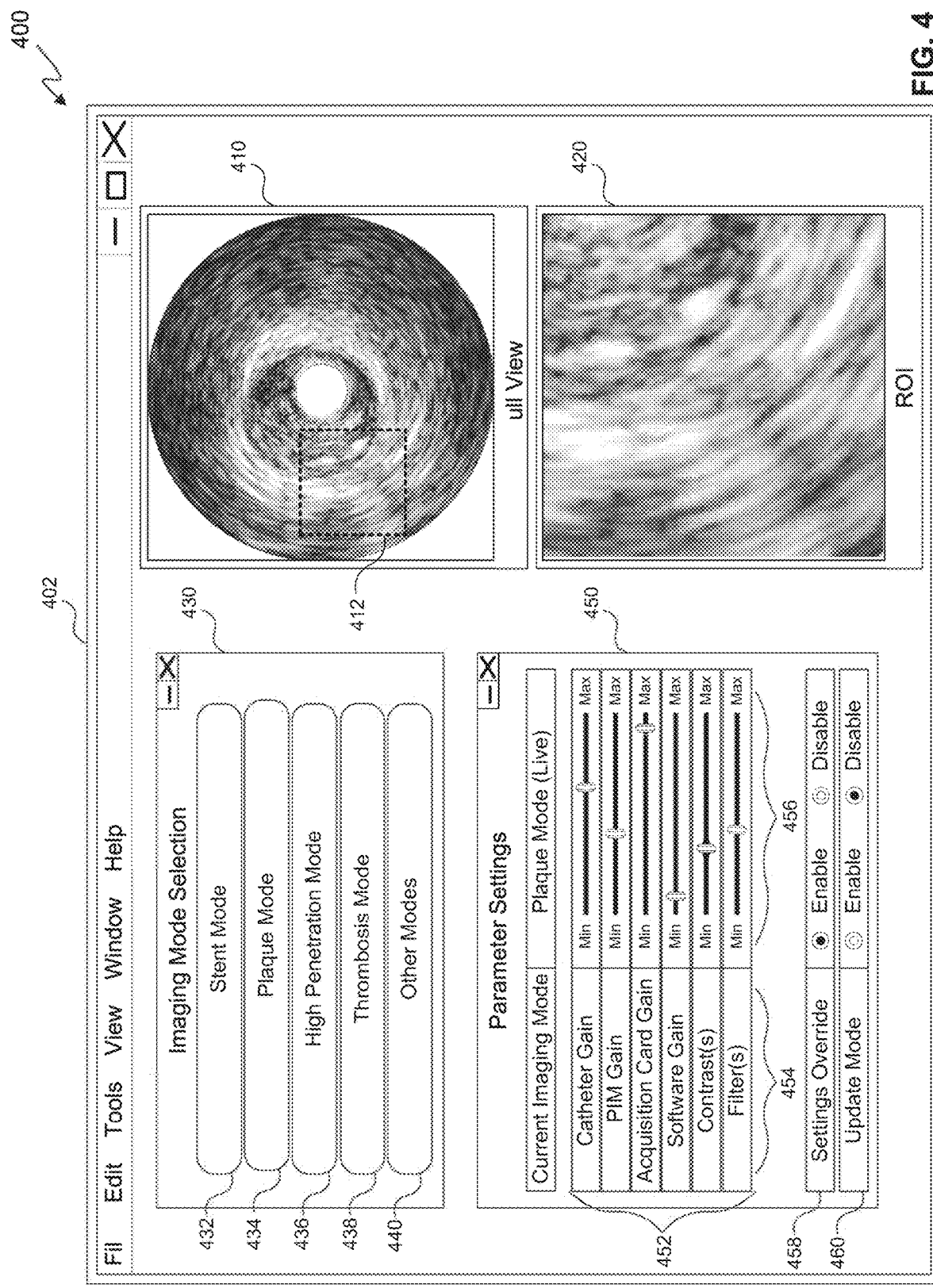
FIG. 4 is a diagram of a medical imaging interface for live image viewing according to some embodiments of the present disclosure.
Figure 5:
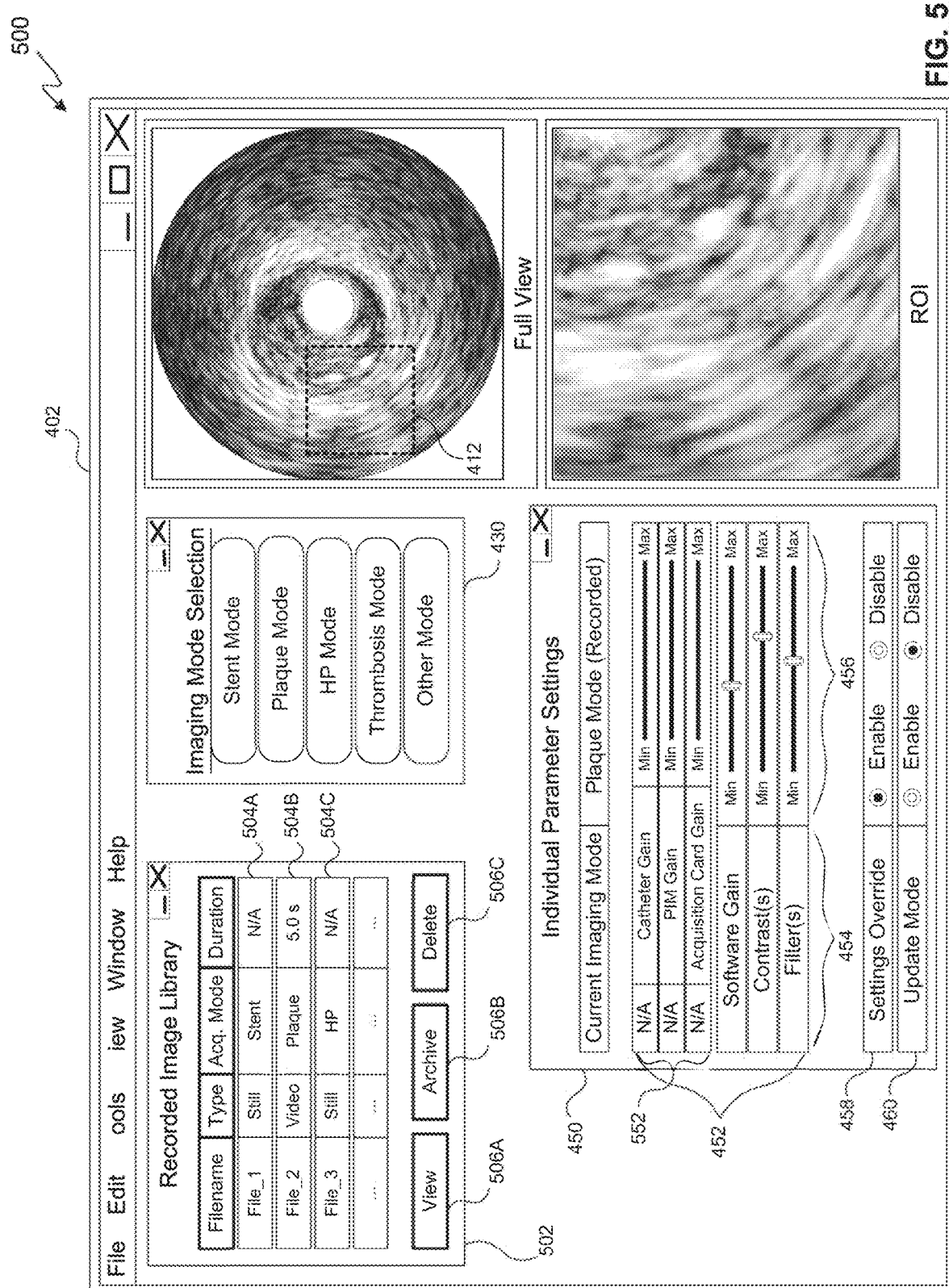
FIG. 5 is a diagram of a medical imaging interface for recorded image viewing according to some embodiments of the present disclosure.

Referring now to FIG. 4, an illustration of a medical imaging system interface 400 is shown. The system interface 400 is a graphical user interface that may be provided by medical imaging system 100 or 200 to a user during an imaging procedure. For example, the system interface 400 may be provided to a user through a display coupled to a controller running a program to enable the collection and processing of imaging data. The display may be a touch-screen display, allowing a user to make selections through the display itself. In embodiments of medical imaging systems in which the display is not a touch-screen display, inputs may be received by the use of a keyboard, mouse, or other input device, such as voice-control.

The system interface 400 includes a main window 402 that includes a number of controls and also presents several sub-windows, which may be adjusted in size so that a given sub-window occupies an entire display or so that it is essentially hidden from a user's view. The main window 402 includes a full view window 410, a region of interest (ROI) window 420, an imaging mode selection window 430, and an individual parameter settings window 450.

The full view window 410 provides the user with a scaled view of imaging data being collected from a target area at a moment. As illustrated, the full view window 410 shows a longitudinal view along a portion of vasculature within a patient. This window 410 may be increased or decreased in size. The full view window 410 also provides a user with the ability to select a region of interest, such as the ROI 412, for display in the ROI window 420. The ROI window 420 may allow for a full resolution view of the ROI 412 selection in the full view window 410 or simply a higher resolution view than in the full view window 410.

The system interface 400 further includes the imaging mode selection window 430. The selection window 430 includes a plurality of groups of settings, or settings groups, that are optimized for viewing a specific feature at the target area. For example, the selection window 430 provides a button to select a stent mode 432 that includes a plurality of settings with parameters set so as to improve the visual depiction of a stent at the target area. This may be used to ensure proper positioning of the stent within the patient. For example, the stent mode 432 may lower gain settings applied by software in programs 212, the acquisition card 208, the PIM 220, and/or the imaging device 230. The contrast may be set higher. In contrast, by selection of a plaque mode 434, or soft tissue mode, a group of parameters may be implemented in various settings so that the gain is increased throughout the imaging pipeline, and the contrast may be set lower. In general, low contrast settings are better for looking at plaque subtleties and blood flow, while high contrast settings are used more for getting clear borders and gross morphology. High contrast is also typically preferred when the physician is sitting far from the display.

Furthermore, because certain elements within the image tend to have similar gray scale levels, boosting the intensity of these levels can emphasize these elements. For example, by boosting the lower intensity signals, it is possible that the appearance of blood could be enhanced. Inversely, by turning down these gray levels, the blood appearance might be de-emphasized.

The settings groups may be optimized such that an overall effect of a setting may be achieved non-uniformly across the pipeline. For example, in lowering the gain when switching from plaque mode 434 to the stent mode 432, more of the decrease may be obtained by a decrease of PIM-related gain than from acquisition card gain in some embodiments. The thrombosis mode 328 may include high gain and time gain compression. These settings are pre-programmed and then accessed by selection of a mode through the selection window 430.

As illustrated, the selection window 430 presents a stent mode 432, a plaque mode 434 (which appears selected in FIG. 4), a high penetration mode 436, a thrombosis mode 438, and may include other modes 440. By selecting any mode on the selection window 430, a user of the medical imaging system may set parameters in a plurality of both pre-acquisition stage settings and post-acquisition stage settings. The implementation of the settings of a particular settings group may be propagated through the imaging pipeline in a number of ways. In some embodiments, parameters are directly communicated from the system interface 400 to the acquisition card 208, the microcontroller 224 of PIM 220, and/or the chip 234 of the imaging device 230. Alternatively, the desired setting may be requested and interpreted by each processor or microcontroller in the pipeline, and then implemented by that processor or microcontroller at its level. For example, a specific gain parameter may be transmitted to the chip 234 or a desired gain setting may be communicated to the chip 234, which then implements a corresponding parameter to achieve that desired gain setting.

In some embodiments, the ability of a user to adjust the parameters of the pipeline may be limited to a selection from the modes presented in the selection window 430. However, in other embodiments, when a mode is selected through the selection window 430, additional information may be presented to the user in a parameter settings window 450. The parameter settings window 450 indicates the current imaging mode, as selected from the selection window 430, and provides further detail. Exemplary settings 452 are displayed in the settings window 450 with a name or identifier 454 of the setting and an indication of the parameter 456 of the setting. In some embodiments, the settings window 450 includes an override selector 458. As illustrated, the override selector 458 is a "radio button" type of interface element, presenting the option to disable or to enable a settings override mode in which a user, having previously selected an imaging mode through the selection window 430, may then modify the pre-programmed settings. The parameter settings window 450 may present all available individual settings with their associated potential parameter values or may only present a subset. By enabling the settings override mode, a user may be able to further tailor the pre-programmed settings associated with the selected imaging mode without having to set each parameter of each setting individually.

In some instances, a user may want to save the fine-tailoring so that the selection of an imaging mode in the selection window 430 includes the tailored setting or settings. The update mode selector 460 is an interface element that allows a user to do this. By enabling the update mode the individually adjusted parameters of the individual settings may be automatically stored for future access by selecting the associated settings mode in the selection window 430. When the update mode is disabled by the update mode selector 460, the tailoring of parameters is not saved and may be undone by selecting a different settings mode from the selection window 430.

Other embodiments of the medical imaging system interface 400 may include different types of interface elements. For example, rather than having slider-type selection elements, which may be continuously adjusted or have discrete positions along the length thereof, to adjust the parameters 456 of the settings 452, other types of user interface elements may be used, such as a dialog box, where a numerical parameter may be entered expressly, or radio buttons, or other elements. Thus, the selections presented to a user by the system interface 400 may provide the functions described above in many different ways. The windows 410, 420, 430, and 450 may be resized relative to each other or hidden. For example, once a user has selected a desired mode, such as high penetration mode 436, the user may collapse or hide the selection window 430 and the parameter settings window 450 and increase the size or the full view window 410 and/or the ROI window 420. The medical imaging system interface 400 may provide a manageable system to a user, allowing that user to make optimized adjustments throughout the imaging pipeline as seen in FIG. 3, including pre-acquisition and post-acquisition stage settings and associated parameters. These optimized adjustments may be excessively complicated and require more familiarity and knowledge of the medical imaging system than a clinician has, but the medical imaging system interface 400 provides a streamlined system for accessing the appropriate settings.

Referring now to FIG. 5, a medical imaging system interface 500 is illustrated. The medical imaging system interface 500 shares many of the features described above in connection with the system interface 400. However, the system interface 500 further includes a recorded image library 502. The recorded image library 502 provides an interface to access a library of saved imaging data, whether "still" images or video, that were recorded earlier. The library 502 may include imaging data obtained months or days before, and may also include imaging data obtained just seconds before. Thus, for example, when a pullback movement is performed to gather imaging data along a length of an artery, the data is stored for subsequent viewing in memory (such as memory 206 of FIG. 2 or remote networked storage) and made accessible through the library 502.

The library 502 includes exemplary files 504A, 504B, and 504C. The library includes a filename, a file type, and a duration for each file. Additionally, the library 502 includes an indication of the acquisition mode that was used in the collection of the associated imaging data. Thus, the filename of the exemplary file 504A is File_1, it is a still image, thus the duration field is not applicable, and the data was acquired using the stent mode as selected in the imaging mode selection window 430. The library 502 permits selection of a file of imaging data and further presents buttons to view, archive, or delete the selected file. The view button 506A may cause the file to be displayed in both the full view window 410 and the ROI window 420 if a ROI 412 is selected. Selection of the archive button 506B may remove the file from the library 502 to an archive from which it may be retrieved later. By selecting the delete button 506C, the selected file is deleted or removed from the library 502 and marked for deletion.

While the imaging mode selection window 430 in the system interface 500 may present the same selections of settings groups or modes to a user as in the system interface 400, the settings window 450 contains some differences. The exemplary settings 452 are illustrated, with a subset 552 of the exemplary settings 452 being indicated as not applicable. As discussed above, after imaging data is collected using an intravascular imaging device, some of the acquisition settings may be altered while others cannot be altered. Post-acquisition stage settings may be altered even after imaging data is stored in a file, while pre-acquisition stage settings may not be altered at all or without computationally intensive reconstruction. Thus, the subset 552 of the exemplary settings 452 includes those settings that are not changeable when viewing recorded images from the library 502. Thus, when selecting from the selection window 430 to apply the associated settings group of the selected mode to the file selected from the library 502, only some of the settings from the selected mode, the post-acquisition settings, may be applied. Like the medical imaging system interface 400, the system interface 500 may facilitate the control of a medical imaging system to allow a user to better view imaging data with a specific type of target subject in mind.

Figure 6:
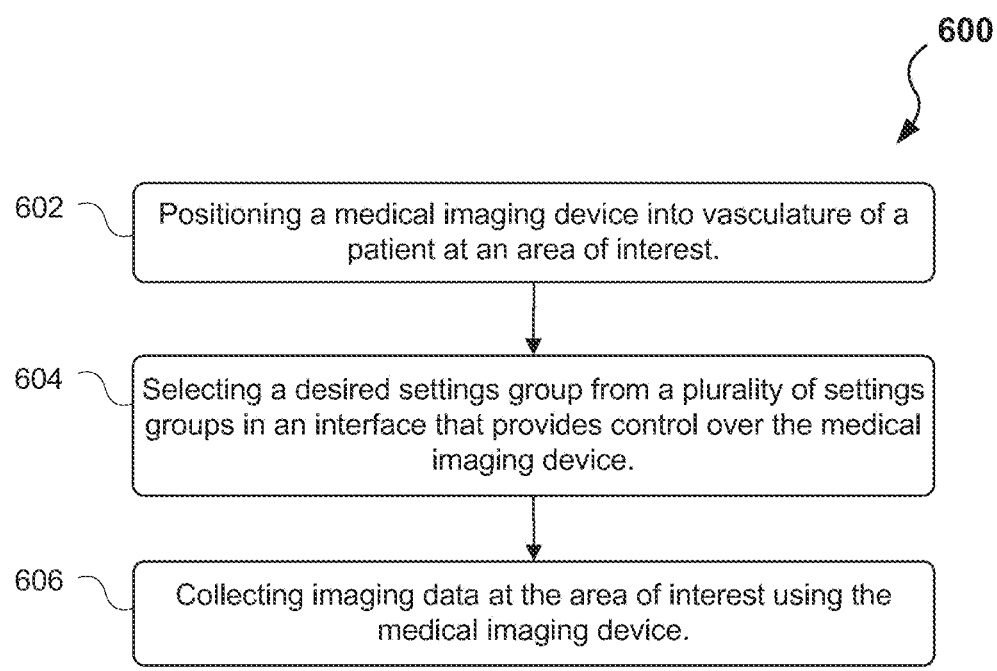
FIG. 6 is a method for optimally viewing medical images according to some embodiments of the present disclosure.

FIG. 6 is a flowchart of a method 600 for optimally viewing intravascularly obtained medical images. The method 600 includes several enumerated steps as illustrated. However, embodiments of the method 600 may include additional steps before, after, and/or in between the enumerated steps. Thus, method 600 may begin in step 602 when a medical imaging device is positioned into vasculature of a patient at an area of interest. The medical imaging device is in communication with a medical imaging system. In step 604, a desired settings group is selected from a plurality of settings groups in a medical imaging system interface that provides control over the medical imaging device. The desired settings group includes parameters affecting acquisition throughout an acquisition pipeline of the medical imaging system. And in step 606, imaging data is collected at the area of interest using the medical imaging device.

To better describe an embodiment of the method 600 reference is made to the medical imaging system 200 of FIG. 2 and to the medical imaging system interface 400 of FIG. 4. Thus, the method 600 may begin when a clinician positions an imaging device 230 into the vasculature of a patient at a target area (step 602). The imaging device 230 may be an IVUS imaging device or an intravascular OCT imaging device. The target area may be a treatment site having a stent inserted and positioned therein.

The user/clinician selects a desired settings group, stent mode 432, using a mouse or other input device, from a plurality of settings groups presented in the selection window 430 (step 604). The stent mode 432 includes a plurality of settings each having a pre-programmed parameter as seen in the parameter settings window 450 of FIG. 4. By selecting the stent mode 432, the user selects the pre-programmed parameters for each of the various settings. These settings are optimized so that the stent may be clearly viewed. Then, after the stent has been adequately observed with the optimized settings, in order to more clearly depict the soft tissue near the stent, the plaque mode 434 may be selected. The selected settings group includes parameters for settings throughout the imaging acquisition pipeline, and thus includes pre-acquisition settings and post-acquisition settings. To implement the settings group, the parameters may be propagated throughout the imaging acquisition pipeline.

When the selected settings group, or mode, is chosen from the selection window 430, the imaging device 230 may be used to collect imaging data at the target area (step 606). This imaging data may be processed and recorded in memory 206 and/or viewed immediately, i.e. viewed live. If processed and recorded, it may be available through the library 502 of the system interface 500 of FIG. 5 as part of the method 600. In general, any of the features described above in connection with the system interfaces 400 and 500 may be employed in various embodiments of the method 600.

Additionally, some embodiments of the system interfaces 400 and 500, which may be part of the imaging systems 100 and 200, include tangible, non-transient, computer-readable media that include executable code that when run by a processor, such one or more processors of the controllers 118 and 120 or the processing system 101 of FIG. 1 or the CPU 204 of FIG. 2, may cause the processor(s) to perform the steps of method 600 as described above. Some common forms of computer-readable media that may include the steps of methods 600 are, for example, floppy disk, flexible disk, hard disk, magnetic tape, any other magnetic medium, CD-ROM, any other optical medium, RAM, ROM, any other memory chip or cartridge, and/or any other medium from which a processor or computer is adapted to read. The computer-readable media may be memory 206 of FIG. 2, which may include instructions that provide the system interfaces 400 and/or 500 when executed by a processor.

The systems 100 and 200, incorporating the system interfaces 400 and/or 500, performing the method 600 may provide a beneficial degree of optimization to a user, permitting the user to easily select the optimal settings for a desired target. The settings require many parameters to be set throughout the imaging pipeline, including some that may otherwise not be presented to the user. Observation of a target area using such systems and methods may be simpler, quicker, and provide more detail of the desired aspects of the area.

The examples provided above are exemplary only and are not intended to be limiting. One skilled in the art may readily devise other systems consistent with the disclosed embodiments which are intended to be within the scope of this disclosure. As such, the application is limited only by the following claims.

What is claimed is:

1. An intravascular imaging system, the system comprising:
   a computer configured to receive a selection of a desired settings group from a plurality of settings groups corresponding respectively to different imaging targets, wherein the desired settings group comprises a plurality of settings suitable for imaging a desired imaging target of the different imaging targets, wherein the plurality of settings correspond respectively to different components of an image acquisition pipeline, wherein the different components of the image acquisition pipeline comprise an intravascular imaging device, a patient interface module (PIM), and the computer;
   the intravascular imaging device, wherein the intravascular imaging device is configured to apply a first setting of the plurality of settings to live image data obtained by the intravascular imaging device while positioned within a blood vessel; and
   the PIM, wherein the PIM is configured to apply a second setting of the plurality of settings to the live image data received from the intravascular imaging device, and
   wherein the computer is configured to execute software to apply a third setting of the plurality of settings to the live image data received from the PTM, and
   wherein the computer is configured to output, to a display, an intravascular image generated from the live image data at the computer.

2. The system of claim 1, wherein the computer comprises a graphics processing unit (GPU).

3. The system of claim 1, wherein the computer comprises an acquisition card.

4. The system of claim 1,
   wherein the computer comprises one or more processors and an acquisition card, and wherein, to apply the third setting of the plurality of settings:
  the acquisition card is configured to apply an acquisition card parameter to the live image data received from the PIM; and
  the one or more processors are configured to apply a software parameter to the live image data received from the acquisition card.

5. The system of claim 1, wherein the intravascular imaging device comprises an intravascular ultrasound (IVUS) imaging device.

6. The system of claim 1, wherein the plurality of settings comprises pre-acquisition parameters and post-acquisition parameters, wherein the pre-acquisition parameters comprise a PIM gain and the post-acquisition parameters comprise a software gain.

7. The system of claim 1, wherein the plurality of settings includes a gain parameter, a time gain compensation (TGC) parameter, a contrast parameter, or a filter parameter.

8. The system of claim 1, wherein the first setting comprises a first gain parameter of the intravascular imaging device, the second setting comprises a second gain parameter of the PIM, and the third setting comprises a third gain parameter of the software executed by the computer.

9. The system of claim 1, wherein the settings groups comprise a stent settings group for viewing a stent and a soft tissue settings group for viewing soft tissue.

10. The system of claim 1, further comprising a database for storing the live image data.

11. The system of claim 10, wherein the computer is configured to:
  record the live image data into a recorded image file stored in the database;
  receive an input to modify the plurality of settings of the desired settings group with respect to the recorded image file;
  apply an alternative plurality of settings to the recorded image file based on the input; and
  output the recorded image file to the display.

12. The system of claim 11, wherein, to apply the alternative plurality of settings to the recorded image file, the computer is configured to:
  adjust only the third setting of the plurality of settings.

13. The system of claim 1, wherein the computer is configured to receive the selection through a bedside controller, a touch screen, a keyboard, or a mouse.

14. The system of claim 1, wherein the computer is configured to receive the selection via a graphical user interface provided on the display.

15. The system of claim 1, further comprising the display.

* * * * *